(12) United States Patent
Schreiber

(10) Patent No.: US 11,602,911 B2
(45) Date of Patent: Mar. 14, 2023

(54) METHOD FOR PRODUCING AN ACCOMMODATIVE INTRAOCULAR LENS

(71) Applicant: Carl Zeiss Meditec AG, Jena (DE)

(72) Inventor: Benjamin Schreiber, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 17/728,385

(22) Filed: Apr. 25, 2022

(65) Prior Publication Data

US 2022/0339896 A1 Oct. 27, 2022

(30) Foreign Application Priority Data

Apr. 27, 2021 (DE) ...................... 10 2021 110 782.2

(51) Int. Cl.
*B29D 11/02* (2006.01)
*A61F 2/16* (2006.01)

(52) U.S. Cl.
CPC .......... *B29D 11/023* (2013.01); *A61F 2/1624* (2013.01); *A61F 2240/001* (2013.01)

(58) Field of Classification Search
CPC ..... B29D 11/023; A61F 2/1624; A61F 2/1635
USPC ...................................................... 156/275.7
See application file for complete search history.

(56) References Cited

U.S. PATENT DOCUMENTS

| | | | |
|---|---|---|---|
| 5,185,107 A | 2/1993 | Blake | |
| 10,802,297 B2* | 10/2020 | Larmagnac | ............ G02C 7/049 |
| 2016/0008126 A1* | 1/2016 | Salahieh | .......... B29D 11/00028 |
| | | | 623/6.22 |
| 2016/0030161 A1* | 2/2016 | Brady | ................... A61F 2/1648 |
| | | | 623/6.13 |

(Continued)

FOREIGN PATENT DOCUMENTS

| | | |
|---|---|---|
| EP | 435525 A2 | 7/1991 |
| EP | 0435525 A2 | 7/1991 |

(Continued)

OTHER PUBLICATIONS

Office Action issued in German Patent Application No. DE 10 2021 110 782.2 (from which this application claims priority), dated Dec. 17, 2021 and English language machine translation thereof.

(Continued)

*Primary Examiner* — Matthew J Daniels
*Assistant Examiner* — Gregory C. Grosso
(74) *Attorney, Agent, or Firm* — Ewers IP Law PLLC; Falk Ewers

(57) ABSTRACT

A method for producing an accommodative intraocular lens includes providing first and second components and a support body with an interior space and open to the top, fastening the first component to the support body, generating pressure which is higher in the exterior space than in the interior space such that the first component deforms downward, producing an adhesive surface on the upper side of the first component and/or on the second component, applying a liquid to the first component from above into the latter's downwardly deformed region, the liquid at no time contacting the adhesive surface, fastening the second component to the first component with the adhesive surface, as a result of which the accommodative intraocular lens is formed and the liquid is encapsulated with the first component and the second component in a cavity arranged in the interior of the intraocular lens.

7 Claims, 2 Drawing Sheets

(56) References Cited

U.S. PATENT DOCUMENTS

2016/0058553 A1 3/2016 Salahieh et al.
2017/0172728 A1* 6/2017 Chen .................... B29D 11/023

FOREIGN PATENT DOCUMENTS

| EP | 0435525 A3 | 7/1991 |
| JP | 2018530003 A | 10/2018 |
| WO | 2011137191 A1 | 11/2011 |
| WO | 2017060537 A2 | 4/2017 |

OTHER PUBLICATIONS

Decision to Grant issued in German Patent Application No. DE 10 2021 110 782.2 (from which this application claims priority), dated Feb. 4, 2022 and English language machine translation thereof.
European Search Report dated Sep. 20, 2022 of European counterpart application No. EP 22167978, and English language translation thereof.
Notice of the Reason for Refusal from Oct. 31, 2022 of Japanese application No. JP2022070636, and English language translation thereof.

* cited by examiner

METHOD FOR PRODUCING AN ACCOMMODATIVE INTRAOCULAR LENS

CROSS REFERENCE TO RELATED APPLICATIONS

This application claims priority to German patent application DE 10 2021 110 782.2, filed Apr. 27, 2021, the entire content of which is incorporated herein by reference.

TECHNICAL FIELD

The disclosure relates to a method for producing an accommodative intraocular lens.

BACKGROUND

Accommodation is understood to mean the ability of the eye to dynamically adapt the refractive power and as a result see objects at different distances in focus. In the process, a change in diameter of the ciliary muscle in the eye is transferred via zonular fibers to a flexible capsular bag, within which a flexible lens is arranged. However, the ability to accommodate deteriorates with increasing age, having presbyopia as a consequence. This is predominantly due to a reducing elasticity of the lens, which solidifies with increasing age. An artificial intraocular lens replaces the lens within the scope of a cataract treatment. By way of example, the intraocular lens may be monofocal, may have a plurality of foci or may have an extended focal range. However, there are also concepts with an accommodative embodiment of the intraocular lens, consequently providing the option of restoring the accommodative ability of the eye. By way of example, the accommodative intraocular lens has a deformable membrane which delimits a fluid-filled cavity in the interior of the intraocular lens. The membrane and the cavity are deformed when the capsular bag deforms, as a result of which the focus of the intraocular lens is displaced and hence it is possible to dynamically adapt the refractive power, like in the case of the natural lens.

Conventionally, the accommodative intraocular lens is produced by virtue of introducing a small incision into the intraocular lens, injecting the fluid into the cavity via the incision, and subsequently sealing the incision again. However, this is a complicated method.

EP 0 435 525 A2 describes a multifocal ophthalmic lens. US 2016/0030161 A1 describes an accommodating intraocular lens.

SUMMARY

It is therefore an object of the disclosure to provide a method for producing an accommodative intraocular lens, the method being easily implementable.

The method according to an aspect of the disclosure for producing an accommodative intraocular lens includes the steps of: a) providing a first component, a second component, and a support body which has an interior space and is open to the top such that the interior space is accessible from above; b) fastening the first component to the support body such that the interior space is delimited by the first component, and the first component separates an exterior space arranged above the first component from the interior space; c) generating a higher pressure in the exterior space than in the interior space such that the first component deforms downward; d) producing an adhesive surface on the upper side of the first component and/or on the second component; e) applying a liquid to the first component from above into the latter's downwardly deformed region, the liquid at no time contacting the adhesive surface; f) fastening the second component to the first component with the adhesive surface, as a result of which the accommodative intraocular lens is formed and the liquid is encapsulated by way of the first component and the second component in a cavity arranged in the interior of the intraocular lens.

If the liquid were to contact the adhesive surface, it would not be possible to fasten the second component to the first component. By virtue of the first component being deformed downward in step c), it is possible to keep the liquid away from the adhesive surface at all times. As a result of the method according to an aspect of the disclosure, it is not necessary to introduce an incision into the accommodative intraocular lens, which incision has to be subsequently sealed again with much outlay, for the purposes of producing the accommodative intraocular lens. Hence, the method according to an aspect of the disclosure for producing the accommodative intraocular lens is easily implementable.

The method typically includes the step of: g) generating the same pressure in the interior space as in the exterior space. As a result, the accommodative intraocular lens can easily be removed from the support body. In this case, it is also conceivable for the method to include the step of: h) generating a higher pressure in the interior space than in the exterior space. As a result, the accommodative intraocular lens can be removed more easily from the support body, or it removes itself from the support body on its own.

It is typical for the first component to have an optics body and the second component to have a membrane. Alternatively, it is typical for the first component to have a membrane and the second component to have an optics body. Alternatively, it is typical for the first component and the second component to each have a membrane. The membrane is deformable and a deformation of the membrane also leads to a deformation of the cavity filled with the liquid. As a result, the focus of the accommodative intraocular lens can be displaced particularly easily.

The membrane is typically gas permeable. Should some gas from the exterior space also be arranged in the cavity together with the liquid, the gas can particularly easily escape the accommodative intraocular lens through the membrane.

It is typical for the gas arranged in the exterior space to contain a noble gas, in particular helium and/or argon, with a volume fraction of at least 80%. Particularly typically, the volume fraction of helium is at least 90%, at least 95%, or at least 99%. Should some gas from the exterior space also be arranged in the cavity together with the liquid, the helium can particularly easily escape the accommodative intraocular lens via the first component and/or the second component.

In step d), the adhesive surface is typically produced by the application of an adhesive. By way of example, the adhesive can be a silicone adhesive. Alternatively, it is typical for the adhesive surface to be produced in step d) by carrying out a surface treatment. The surface treatment particularly typically includes a plasma treatment. By way of example, the plasma may contain ionized oxygen.

The support body is typically heated in step f). This can accelerate curing of the adhesive, or the second component can be fastened more quickly to the first component with the adhesive surface produced by the surface treatment.

Step d) is typically carried out before step e). Alternatively, step e) is typically carried out before step d).

In the range of visible light, the liquid typically has a higher refractive index than water. It is also conceivable for the refractive index of the liquid to equal the refractive index of the first component and/or of the second component. As a result, it is possible to avoid reflection losses at the transition from the liquid to the first component and/or to the second component.

The support body is typically substantially ring shaped. The support body may be configured to be open at its lower end, particularly if the atmosphere in the interior space is aspirated in step c). Alternatively, it is conceivable that the support body has a closed embodiment apart from its upper end, particularly if the pressure in the exterior space is increased in step c).

It is typical for the first component to be fastened to the upper end of the support body in step b).

It is typical for a plurality of support bodies and, for each support body, a respective first component and a respective second component to be provided in step a) and for a plurality of accommodative intraocular lenses to be produced simultaneously within the scope of the method. As a result of the simultaneous production of the plurality of accommodative intraocular lenses, the method can be carried out in a cost-effective manner.

BRIEF DESCRIPTION OF THE DRAWINGS

The disclosure will now be described with reference to the drawings wherein.

DESCRIPTION OF EXEMPLARY EMBODIMENTS

Figure 1:
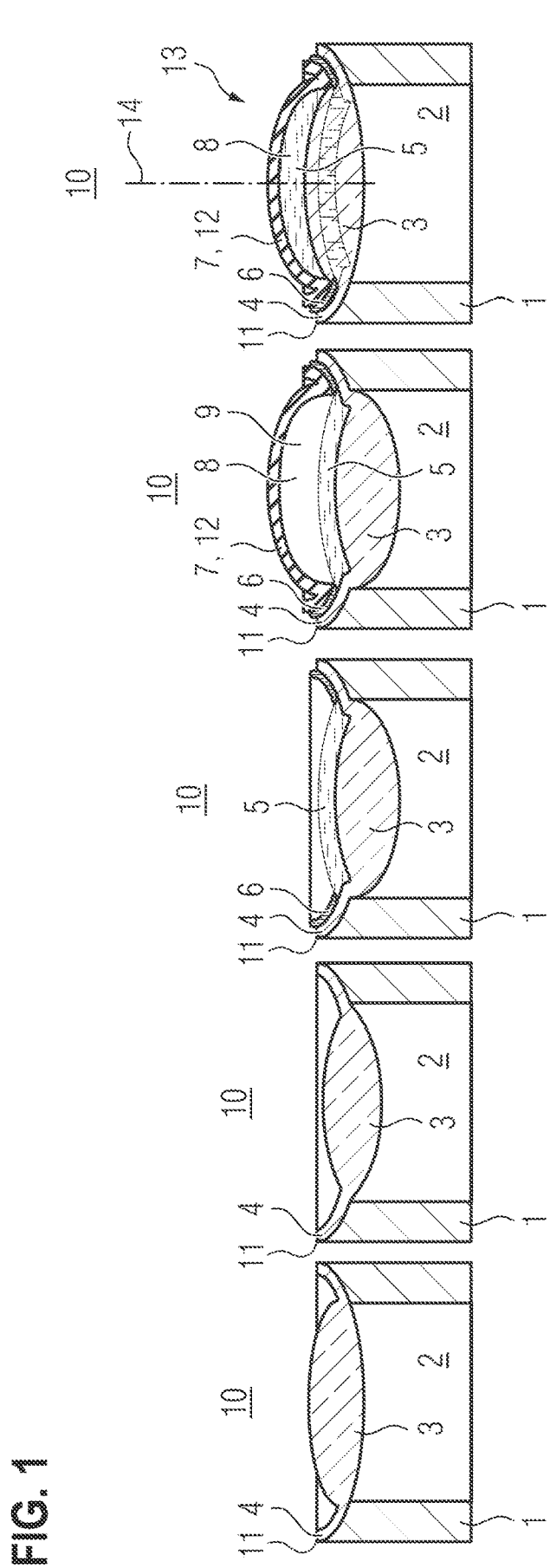
FIG. 1 shows a method according to a first exemplary embodiment of the disclosure.
Figure 2:
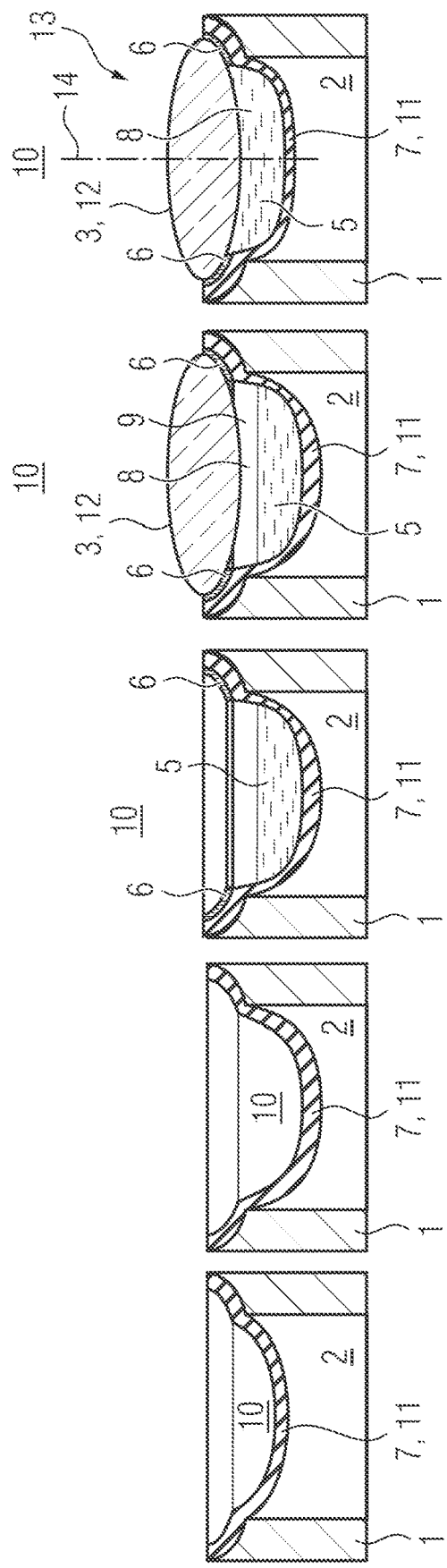
FIG. 2 shows a method according to a second exemplary embodiment of the disclosure.

FIGS. 1 and 2 show the method five different times, with time advancing from left to right. The method for producing an accommodative intraocular lens 13 includes the steps of: a) providing a first component 11, a second component 12, and a support body 1 which has an interior space 2 and is open to the top such that the interior space 2 is accessible from above; b) fastening the first component 11 to the support body 1 such that the interior space 2 is delimited by the first component 11 and the first component 11 separates an exterior space 10 arranged above the first component 11 from the interior space 2, see the respective first time in FIGS. 1 and 2; c) generating a higher pressure in the exterior space 10 than in the interior space 2 such that the first component 11 deforms downward, as shown at the second time in FIGS. 1 and 2; d) producing an adhesive surface 6 on the upper side of the first component 11, cf. the third time in FIGS. 1 and 2, it alternatively or additionally being possible to produce the adhesive surface on the second component 12; e) applying a liquid 5 to the first component 11 from above into the latter's downwardly deformed region, the liquid 5 at no time contacting the adhesive surface 6, see the third time in FIGS. 1 and 2; f) fastening the second component 12 to the first component 11 with the adhesive surface 6, as a result of which the accommodative intraocular lens 13 is formed and the liquid 5 is encapsulated by way of the first component 11 and the second component 12 in a cavity 8 arranged in the interior of the intraocular lens 13, see the fourth time in FIGS. 1 and 2. Moreover, the method can include the step of: generating the same pressure in the interior space 2 as in the exterior space 10 after the completion of step f), cf. the fifth time in FIGS. 1 and 2.

FIGS. 1 and 2 show that the first component 11 can be fastened to the upper end of the support body 1 in step b). The upper end can be configured with flanks that slope inward and downward, as shown in FIGS. 1 and 2. This is particularly advantageous if the first component 11, as shown in FIGS. 1 and 2, has a convex form at its lower end. Then, the upper end of the support body 1 has a concave form. Alternatively, it is conceivable for the upper end of the support body 1 to have a non-arched plane, that is to say a flat plane, which typically extends horizontally and is formed with horizontal surfaces.

In step b), the first component 11 is fastened to the support body 1 in such a way that there cannot be a gas exchange between the interior space 2 and the exterior space 10.

The interior space 2 reduces in size by virtue of the first component 11 deforming downward in step c). By way of example, the pressure in the interior space 2 can be less than the pressure in the exterior space 10 by at least 10 kPa such that the first component 11 deforms sufficiently. By way of example, the pressure in the interior space 2 can be less than the pressure in the exterior space 10 by no more than 100 kPa such that damage to the accommodative intraocular lens 13 can be avoided.

It is possible in step c) to increase the pressure in the exterior space 10 and/or lower the pressure in the interior space 2. The lower end of the support body 1 may be open. As a result, the pressure in the interior space 2 can be lowered by aspirating the atmosphere via the lower end of the support body 1. Alternatively, it is conceivable for the lower end of the support body 1 to be closed and for the only opening of the support body 1 to be provided at its upper end. In this case, the pressure in the exterior space 10 should be increased in step c). The support body 1 can be substantially ring shaped at least in sections, independently of whether the support body 1 has an open or closed form at its lower end.

Both carrying out step d) before step e) and carrying out step e) before step d) are possible. In both cases, the downward deformation of the first component 11 renders keeping the liquid 5 away from the adhesive surface 6 until the second component 12 is fastened to the first component 11 completely unproblematic. In step d), the adhesive surface 6 can typically be produced by the application of an adhesive. By way of example, the adhesive can be a silicone adhesive. In another example, the adhesive surface 6 can be produced in step d) by carrying out a surface treatment on the first component 11 and/or the second component 12. The surface treatment may include a plasma treatment, the plasma for example being able to contain ionized oxygen.

By way of example, the adhesive surface 6 may substantially have the shape of a circular ring. The liquid 5 may be arranged within the circular ring.

The liquid 5 may be transparent to visible light. Moreover, the viscosity of the liquid 5 may be no more than $2*10^3$ Pa*s, as a result of which a good deformability of the accommodative intraocular lens 13 is achieved. By way of example, the liquid can be a silicone oil or substantially consist of the silicone oil. Moreover, in the range of visible light, the liquid 5 can typically have a higher refractive index than water.

The support body 1 can be heated in step f) to accelerate the fastening of the second component 12 to the first component.

In the first exemplary embodiment of the method shown in FIG. 1, the first component 11 has an optics body 3 and the second component 12 has a membrane 7. In the second exemplary embodiment of the method shown in FIG. 2, the first component 11 has a membrane 7 and the second component 12 has an optics body 3. The membrane 7 can be gas permeable. As a result, should a gas 9 reach the cavity 8 from the exterior space 10 in step f), said gas can escape the accommodative intraocular lens 13. The gas 9 arranged in the exterior space 10 may contain helium with a volume fraction of at least 80%, at least 90%, or at least 99%. Helium is a gas that escapes the accommodative intraocular lens 13 particularly quickly through the membrane 7. By way of example, the thickness of the membrane 7 may range from 20 µm to 200 µm or from 20 µm to 150 µm.

As is evident from FIG. 1, the accommodative intraocular lens 13 may include a haptic 4 or a plurality of haptics 4, which are fastened to the optics body 3. Should the first component 11 contain the optics body 3, the haptic 4 or the haptics 4 are part of the first component 11. Should the second component 12 contain the optics body 3, the haptic 4 or the haptics 4 are part of the second component 12. The material of the first component 11 and/or of the second component 12 (the haptics are not depicted in FIG. 2) may contain an acrylic polymer or substantially consist of the acrylic polymer.

To deform the accommodative intraocular lens 13 following an implantation of the accommodative intraocular lens, it is conceivable for the accommodative intraocular lens 13 to include a plurality of bending elements (not depicted in FIGS. 1 and 2), which are arranged on the outside of the membrane 7 in uniform fashion about an optical axis 14 of the accommodative intraocular lens 13. A substantially cylindrical body (not depicted in FIGS. 1 and 2) can be placed on the bending elements following the implantation of the accommodative intraocular lens 13 in the capsular bag of an eye, and said cylindrical body can transfer a force from the capsular bag to the bending elements, leading to the membrane 7 and the cavity 8 deforming.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Support body
2 Interior space
3 Optics body
4 Haptic
5 Liquid
6 Adhesive surface
7 Membrane
8 Cavity
9 Gas
10 Exterior space
11 First component
12 Second component
13 Accommodative intraocular lens
14 Optical axis

What is claimed is:

1. A method for producing an accommodative intraocular lens, the method comprising:
   (a) providing a first component, a second component, and a support body which has an interior space and which is open to the top such that the interior space is accessible from above;
   (b) fastening the first component to the support body such that the interior space is delimited by the first component and the first component separates an exterior space arranged above the first component from the interior space;
   (c) generating a first pressure in the exterior space and a second pressure in the interior space such that the first component deforms downward, wherein the first pressure is higher than the second pressure;
   (d) producing an adhesive surface on the upper side of the first component and/or on the second component;
   (e) applying a liquid to the first component from above into a downwardly deformed region of the first component, the liquid at no time contacting the adhesive surface; and
   (f) fastening the second component to the first component with the adhesive surface, thereby forming the accommodative intraocular lens and encapsulating the liquid with the first component and the second component in a cavity arranged in the interior of the accommodative intraocular lens,
   wherein the first component has an optics body and the second component has a membrane, or
   wherein the first component has the membrane and the second component has the optics body,
   wherein the membrane is gas permeable, and
   wherein, in step (f), gas entered the cavity from the exterior space escapes from the intraocular lens through the membrane.

2. The method as claimed in claim 1, wherein the gas arranged in the exterior space is helium with a volume fraction of at least 80%.

3. The method as claimed in claim 1, wherein the adhesive surface is produced in step (d) by an application of an adhesive.

4. The method as claimed in claim 1, wherein the adhesive surface is produced in step (d) by carrying out a surface treatment, the surface treatment including a treatment with a plasma.

5. The method as claimed in claim 1, wherein the support body is heated in step (f).

6. The method as claimed in claim 1, wherein the support body is ring shaped.

7. The method as claimed in claim 1, wherein the first component is fastened to the upper end of the support body in step (b).

* * * * *